United States Patent
Espino

(10) Patent No.: US 6,202,647 B1
(45) Date of Patent: Mar. 20, 2001

(54) SHOULDER RESTRAINT APPARATUS

(76) Inventor: George V. Espino, P.O. Box 5204, Lansing, IL (US) 60438

(*) Notice: Subject to any disclaimer, the term of this patent is extended or adjusted under 35 U.S.C. 154(b) by 0 days.

(21) Appl. No.: 09/352,902

(22) Filed: Jul. 15, 1999

(51) Int. Cl.⁷ .................................................. A61B 19/00
(52) U.S. Cl. ......................................... 128/869; 128/876
(58) Field of Search ................................. 128/869–876; 602/32–40

(56) References Cited

U.S. PATENT DOCUMENTS

| | | | |
|---|---|---|---|
| 2,848,993 | * | 8/1958 | Terrell. |
| 3,641,997 | * | 2/1972 | Posey, Jr.. |
| 3,701,395 | * | 10/1972 | Theobald ............................ 128/845 |
| 4,524,768 | * | 6/1985 | Serrao. |
| 4,685,454 | * | 8/1987 | Posey. |
| 4,744,354 | * | 5/1988 | Triunfol. |
| 4,911,426 | * | 3/1990 | Scales ................................ 128/845 |
| 4,947,870 | * | 8/1990 | Larcher ............................. 128/869 |
| 5,522,404 | * | 6/1996 | Williams. |
| 5,526,824 | * | 6/1996 | McAllister. |

* cited by examiner

Primary Examiner—Michael A. Brown

(57) ABSTRACT

A patient restraint apparatus includes a restraint strap unit which includes a pair of restraint strap ends, a pair of intermediate restraint strap portions connected to the pair of restraint strap ends, a central restraint strap portion connected between the pair of restraint strap portions, and a pair of strap connectors connected to the pair of restraint strap ends. A pair of tie up strap units are connected to the pair of strap connectors. The pair of strap connectors includes a pair of first buckle members. Each of the tie up strap units includes a second buckle member for connection to a respective first buckle member. Each of the tie up strap units includes a tie strap for tying onto the bed frame. With another embodiment of the invention, the tie strap includes a pair of strap portions that pass through a strap reception channel in one of the second buckle members. The restraint strap ends and portions of the restraint strap portions are in the form of loops. The loops are attached to other portions of the restraint strap portions by sewn stitches.

7 Claims, 4 Drawing Sheets

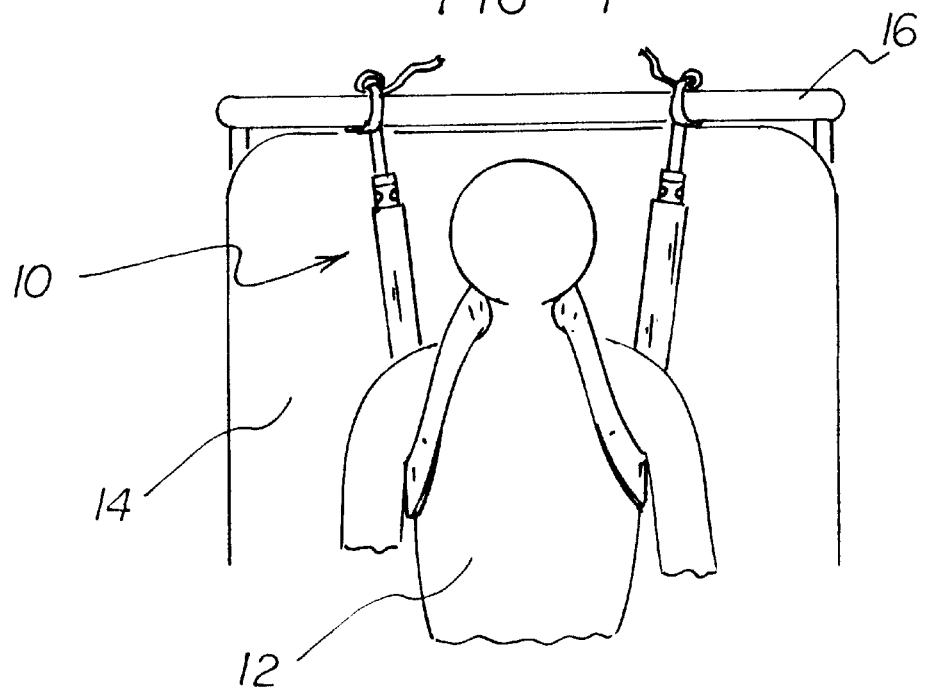
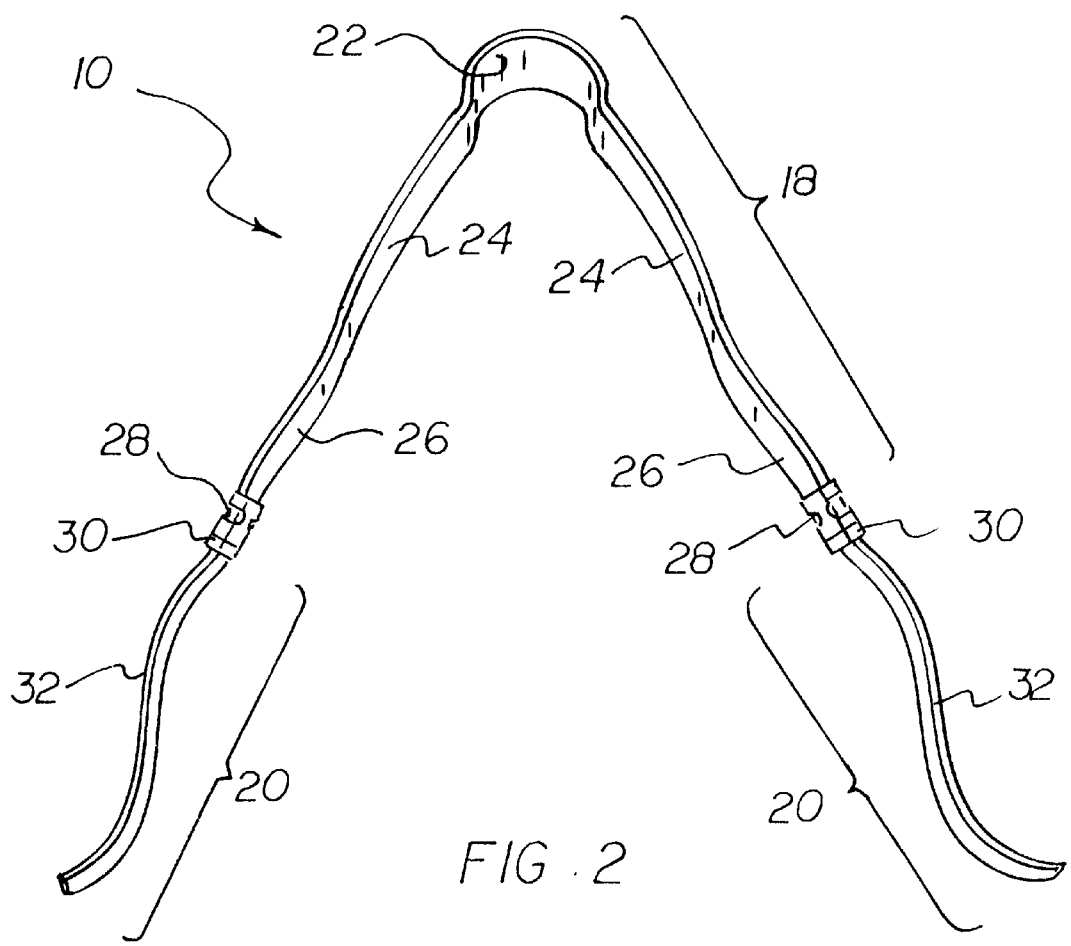

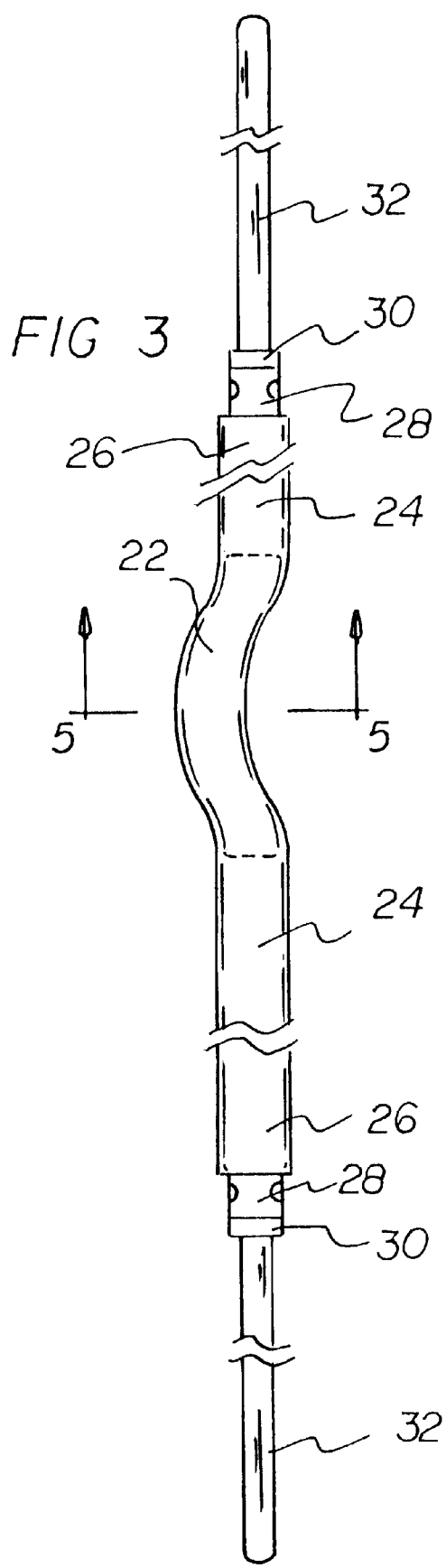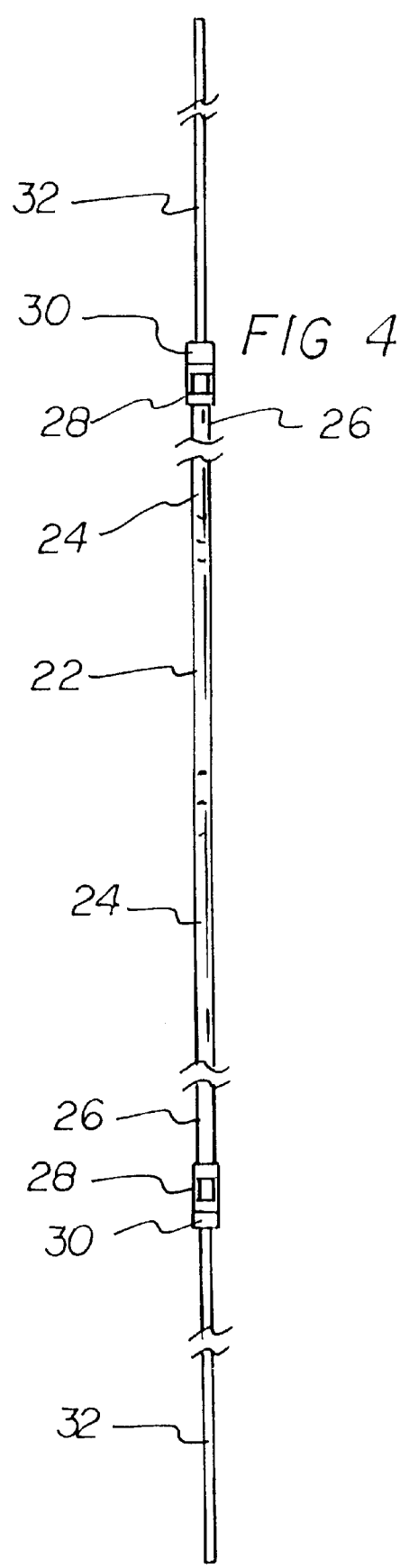

SHOULDER RESTRAINT APPARATUS

BACKGROUND OF THE INVENTION

1. Field of the Invention

The present invention relates generally to restraints for patients and, more particularly, to a restraint especially adapted for restraining a patient to a bed.

2. Description of the Prior Art

It is well known that under certain circumstances a patient must be restrained on a bed. In this respect, throughout the years, a number of innovations have been developed relating to such patient restraints, and the following U.S. patents are representative of some of those innovations: U.S. Pat. Nos. 2,848,993, 3,641,997, 4,524,768, 4,685,454, 4,744,354, 5,522,404, and 5,526,824. More specifically, U.S. Pat. No. 2,848,993 discloses a restraining device which includes wrist straps. Often when a patient is restrained on a bed it is desirable for the patient's hands and wrists to be free of restraint. In this respect, it would be desirable if a patient restraint device were provided which does not employ wrist straps.

U.S. Pat. No. 3,641,997 discloses a restraining device which employs a jacket and a waist strap. Often when a patient is restrained on a bed it is desirable for the patient's waist to be free of restraint. In this respect, it would be desirable if a restraining device were provided which does not employ a waist strap.

Each of U.S. Pat. Nos. 4,524,768, 4,685,454, and 4,744,354 discloses a restraining device which employs a jacket which is worn by a patient. Wearing of a jacket can pose a number of problems, one of which is restricted access to a patient's back. In this respect, it would be desirable if a patient restraining device were provided which does not employ a jacket.

U.S. Pat. No. 5,522,404 discloses a safety harness which includes a strap that encircles a patient's chest. When it would be desirable to have clear access to a patient's without interference from a chest-encircling strap, such a safety harness may pose a problem. In this respect, it would be desirable if a patient restraining device were provided that does not include a chest-encircling strap.

U.S. Pat. No. 5,526,824 discloses a modular restraint system that employs a plurality of modular components for encircling a plurality of body parts. Rather than dealing with the complexities of encircling one or more body parts, it would be desirable if a patient restraint system were provided which does not employ any straps that encircle any body parts.

Thus, while the foregoing body of prior art indicates it to be well known to use patient restraining devices, the prior art described above does not teach or suggest a shoulder restraint apparatus which has the following combination of desirable features: (1) does not employ wrist straps; (2) does not employ a waist strap; (3) does not employ a jacket; (4) does not include a chest-encircling strap; and (5) does not employ any straps that encircle any body parts. The foregoing desired characteristics are provided by the unique shoulder restraint apparatus of the present invention as will be made apparent from the following description thereof. Other advantages of the present invention over the prior art also will be rendered evident.

SUMMARY OF THE INVENTION

To achieve the foregoing and other advantages, the present invention, briefly described, provides a patient restraint apparatus which includes a restraint strap unit which includes a pair of restraint strap ends, a pair of intermediate restraint strap portions connected to the pair of restraint strap ends, a central restraint strap portion connected between the pair of restraint strap portions, and a pair of strap connectors connected to the pair of restraint strap ends. A pair of tie up strap units are connected to the pair of strap connectors.

The pair of strap connectors includes a pair of first buckle members. Each of the tie up strap units includes a second buckle member for connection to a respective first buckle member. Each of the tie up strap units includes a tie strap for tying onto the bed frame.

With another embodiment of the invention, the tie strap includes a pair of strap portions that pass through a strap reception channel in one of the second buckle members. The restraint strap ends and portions of the restraint strap portions are in the form of loops. The loops are attached to other portions of the restraint strap portions by sewn stitches.

The above brief description sets forth rather broadly the more important features of the present invention in order that the detailed description thereof that follows may be better understood, and in order that the present contributions to the art may be better appreciated. There are, of course, additional features of the invention that will be described hereinafter and which will be for the subject matter of the claims appended hereto.

In this respect, before explaining at least two preferred embodiments of the invention in detail, it is understood that the invention is not limited in its application to the details of the construction and to the arrangements of the components set forth in the following description or illustrated in the drawings. The invention is capable of other embodiments and of being practiced and carried out in various ways. Also, it is to be understood, that the phraseology and terminology employed herein are for the purpose of description and should not be regarded as limiting.

As such, those skilled in the art will appreciate that the conception, upon which disclosure is based, may readily be utilized as a basis for designing other structures, methods, and systems for carrying out the several purposes of the present invention. It is important, therefore, that the claims be regarded as including such equivalent constructions insofar as they do not depart from the spirit and scope of the present invention.

It is therefore an object of the present invention to provide a new and improved shoulder restraint apparatus which has all of the advantages of the prior art and none of the disadvantages.

It is another object of the present invention to provide a new and improved shoulder restraint apparatus which may be easily and efficiently manufactured and marketed.

It is a further object of the present invention to provide a new and improved shoulder restraint apparatus which is of durable and reliable construction.

An even further object of the present invention is to provide a new and improved shoulder restraint apparatus which is susceptible of a low cost of manufacture with regard to both materials and labor, and which accordingly is then susceptible of low prices of sale to the consuming public, thereby making such shoulder restraint apparatus available to the buying public.

Still yet a further object of the present invention is to provide a new and improved shoulder restraint apparatus which does not employ wrist straps.

Still another object of the present invention is to provide a new and improved shoulder restraint apparatus that does not employ a waist strap.

Yet another object of the present invention is to provide a new and improved shoulder restraint apparatus which does not employ a jacket.

Even another object of the present invention is to provide a new and improved shoulder restraint apparatus that does not include a chest-encircling strap.

Still a further object of the present invention is to provide a new and improved shoulder restraint apparatus which does not employ any straps that encircle any body parts.

These together with still other objects of the invention, along with the various features of novelty which characterize the invention, are pointed out with particularity in the claims annexed to and forming a part of this disclosure. For a better understanding of the invention, its operating advantages and the specific objects attained by its uses, reference should be had to the accompanying drawings and descriptive matter in which there are illustrated preferred embodiments of the invention.

BRIEF DESCRIPTION OF THE DRAWINGS

The invention will be better understood and the above objects as well as objects other than those set forth above will become more apparent after a study of the following detailed description thereof. Such description makes reference to the annexed drawing wherein:

FIG. 1 is a top view showing a first embodiment of the shoulder restraint apparatus of the invention in use restraining a patient on a bed, wherein the patient is secured to a headboard portion of a bed frame.

FIG. 2 is a top view of the embodiment of the shoulder restraint apparatus shown in FIG. 1 removed from the patient and the bed frame and resting on an edge of the apparatus.

FIG. 3 is a top view of the embodiment of the shoulder restraint apparatus of FIG. 2 stretched out in a straight line.

FIG. 4 is a side view of the embodiment of the invention shown in FIG. 3.

DESCRIPTION OF THE PREFERRED EMBODIMENT

Figure 5:
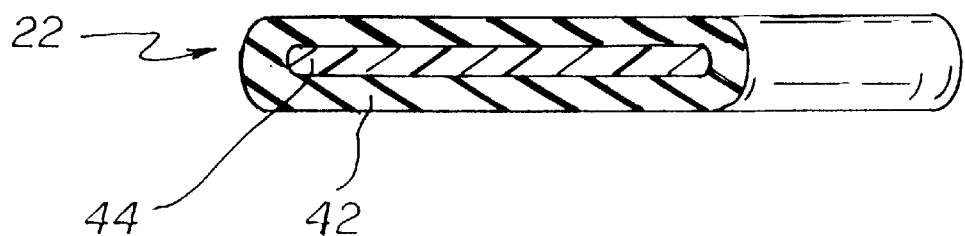
FIG. 5 is an enlarged partial cross-sectional view of the embodiment of the invention shown in FIG. 3 taken along line 5—5 thereof

With reference to the drawings, a new and improved shoulder restraint apparatus embodying the principles and concepts of the present invention will be described.

Turning to FIGS. 1–6, there is shown a first embodiment of the shoulder restraint apparatus of the invention generally designated by reference numeral 10. In the first embodiment shoulder restraint apparatus 10 includes a restraint strap unit 18 which includes a pair of restraint strap ends 26, a pair of intermediate restraint strap portions 24 connected to the pair of restraint strap ends 26, a central restraint strap portion 22 connected between the pair of restraint strap portions 24, and a pair of strap connectors connected to the pair of restraint strap ends 26. A pair of tie up strap units 20 are connected to the pair of strap connectors.

Briefly, to use the patient restraint apparatus 10 of the invention, the restraint strap unit 18 is placed on a patient 12 who is lying on a bed 14, and the tie up strap units 20 are fastened to a portion of a bed frame 16 that is adjacent to the head of the patient 12.

More specifically, as shown in the embodiment of the invention illustrated in FIGS. 1–6, the pair of strap connectors includes a pair of first buckle members 28. Each of the tie up strap units 20 includes a second buckle member 30 for connection to a respective first buckle member 28. Each of the tie up strap units 20 includes a tie strap 32 for tying onto the bed frame 16.

As shown in FIG. 1, to use the patient restraint apparatus 10 of the invention on a patient 12 who is lying on one's back on a bed 14, the central restraint strap portion 22 of the patient restraint apparatus 10 is placed on the backside of the patient's neck. Each of the restraint strap portions 24 are threaded across a top and front portion of one of the patient's shoulders, under an armpit, and back upward under a rear portion of a respective shoulder. The first buckle members 28 are connected to the second buckle member 30, and the tie straps 32 are tied to the bed frame 16.

Figure 6:
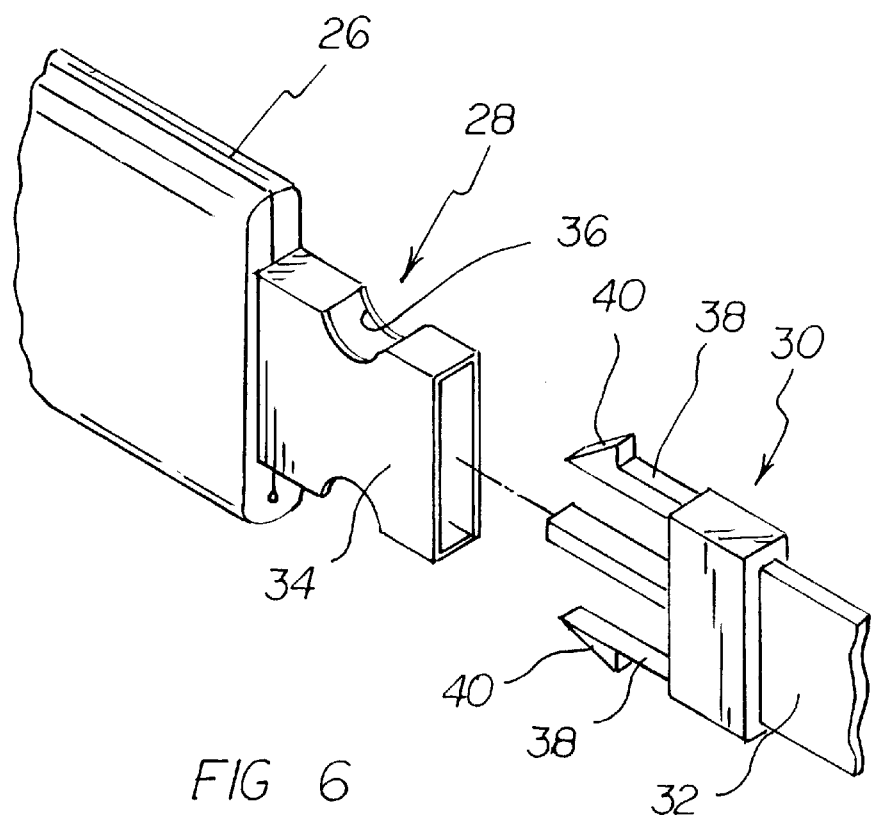
FIG. 6 is an enlarged, partially exploded perspective view of the buckle portion of the embodiment of the invention shown in encircled portion 6 of FIG. 5.

As shown in FIG. 6, each of the first buckle members 28 includes a prong reception channel 34 which includes barb reception apertures 36. Also, each of the second buckle members 30 includes a plurality of prongs 38 which includes barbs 40. When a first buckle member 28 and a second buckle member 30 are connected together, the barbs 40 and prongs 38 enter the prong reception channel 34, and the barbs 40 extend through the barb reception apertures 36 to secure the respective second buckle member 30 to the respective first buckle member 28.

As shown in FIG. 5, the central restraint strap portion 22 includes an interior strap portion 44 and an exterior foam jacket 42.

Figure 7:
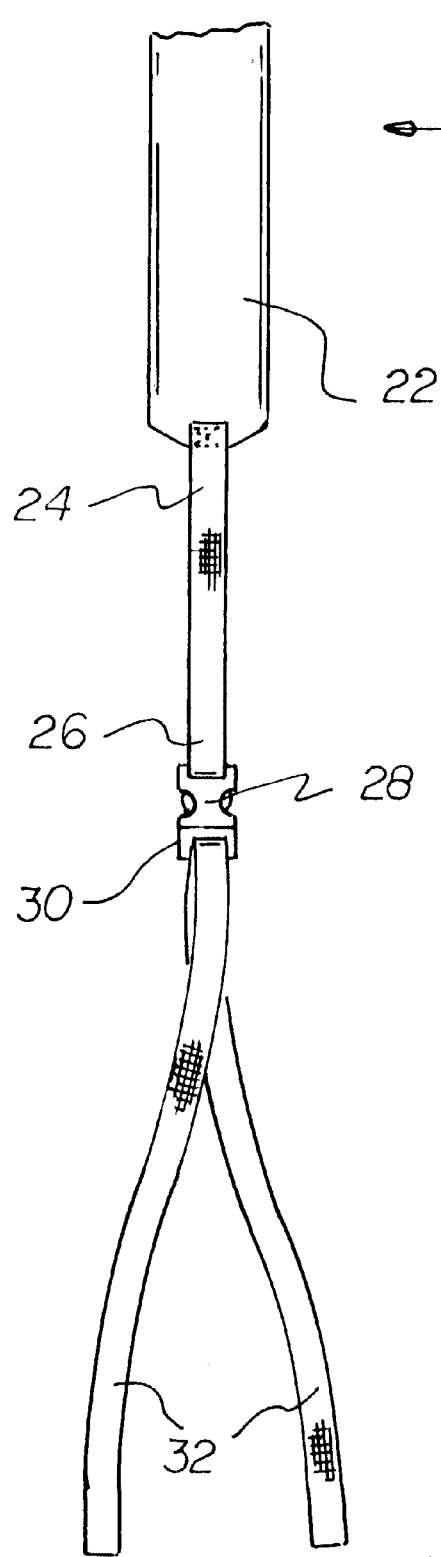
FIG. 7 is a partial top view of a second embodiment of the invention.
Figure 8:
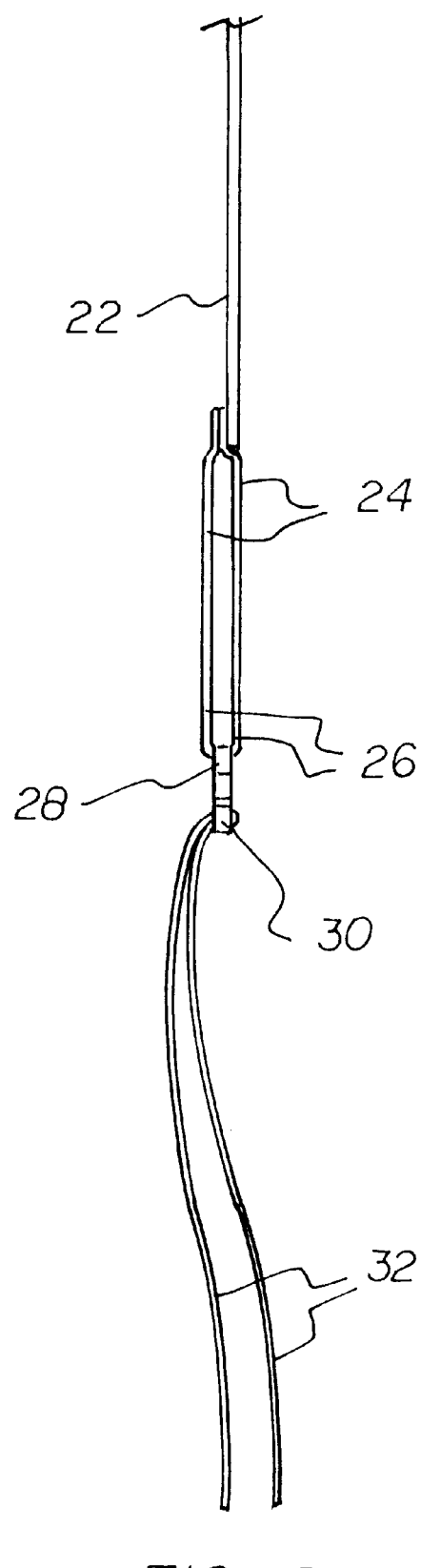
FIG. 8 is a side view of the embodiment of the invention shown in FIG. 7.

Another embodiment of the invention is shown in FIGS. 7 and 8. The tie strap 32 includes a pair of strap portions that pass through a strap reception channel in one of the second buckle members 30. The restraint strap ends 26 and first areas of the restraint strap portions 24 are in the form of loops. The loops are attached to second areas of the restraint strap portions 24 by sewn stitches. To attach the second embodiment of the invention to a bed frame 16, the pair of strap portions are tied to the bed frame 16.

The components of the shoulder restraint apparatus of the 92 invention can be made from inexpensive and durable metal, plastic, and fabric materials.

As to the manner of usage and operation of the instant invention, the same is apparent from the above disclosure, and accordingly, no further discussion relative to the manner of usage and operation need be provided.

It is apparent from the above that the present invention accomplishes all of the objects set forth by providing a new and improved shoulder restraint apparatus that is low in cost, relatively simple in design and operation, and which may advantageously be used without employing wrist straps. With the invention, a shoulder restraint apparatus is provided which does not employ a waist strap. With the invention, a shoulder restraint apparatus is provided which does not employ a jacket. With the invention, a shoulder restraint apparatus is provided which does not include a chest-encircling strap. With the invention, a shoulder restraint apparatus is provided which does not employ any straps that encircle any body parts.

Thus, while the present invention has been shown in the drawings and fully described above with particularity and detail in connection with what is presently deemed to be the most practical and preferred embodiment(s) of the invention, it will be apparent to those of ordinary skill in the art that many modifications thereof may be made without departing from the principles and concepts set forth herein, including, but not limited to, variations in size, materials, shape, form, function and manner of operation, assembly and use.

Hence, the proper scope of the present invention should be determined only by the broadest interpretation of the appended claims so as to encompass all such modifications as well as all relationships equivalent to those illustrated in the drawings and described in the specification.

Finally, it will be appreciated that the purpose of the annexed Abstract is to enable the U.S. Patent and Trademark Office and the public generally, and especially the scientists, engineers and practitioners in the art who are not familiar with patent or legal terms or phraseology, to determine quickly from a cursory inspection the nature and essence of the technical disclosure of the application. Accordingly, the Abstract is neither intended to define the invention or the application, which only is measured by the claims, nor is it intended to be limiting as to the scope of the invention in any way.

What is claimed as being new and desired to be protected by Letters Patent of the United States is as follows:

1. A patient restraint apparatus, comprising:

a restraint strap unit which includes a pair of restraint strap ends, a pair of intermediate restraint strap portions connected to said pair of restraint strap ends, a central restraint strap portion connected between said pair of restraint strap portions, and a pair of strap connectors connected to said pair of restraint strap ends, and a pair of tie up strap units connected to said pair of strap connectors.

2. The apparatus of claim 1 wherein said pair of strap connectors include a pair of first buckle members.

3. The apparatus of claim 2 wherein each of said tie up strap units includes a second buckle member for connection to a respective first buckle member.

4. The apparatus of claim 2 wherein each of said tie up strap units includes a tie strap for tying onto the bed frame.

5. The apparatus of claim 3 wherein each of said tie strap includes a pair strap portions that pass through a strap reception channel in said second buckle member.

6. The apparatus of claim 1 wherein said restraint strap ends and first areas of said restraint strap portions are in forms of loops.

7. The apparatus of claim 6 wherein said loops are attached to second areas of said restraint strap portions by sewn stitches.

* * * * *